(12) United States Patent
Rocha de Faria et al.

(10) Patent No.: US 11,589,861 B2
(45) Date of Patent: Feb. 28, 2023

(54) MENISCUS SUTURE DEVICE

(71) Applicants: José Leonardo Rocha de Faria, Rio de Janeiro (BR); Bernardo Augusto Rocha de Faria, Juiz de Fora (BR); Alan de Paula Mozella, Rio de Janeiro (BR)

(72) Inventors: José Leonardo Rocha de Faria, Rio de Janeiro (BR); Bernardo Augusto Rocha de Faria, Juiz de Fora (BR); Alan de Paula Mozella, Rio de Janeiro (BR)

(*) Notice: Subject to any disclaimer, the term of this patent is extended or adjusted under 35 U.S.C. 154(b) by 430 days.

(21) Appl. No.: 16/799,372

(22) Filed: Feb. 24, 2020

(65) Prior Publication Data

US 2021/0128147 A1 May 6, 2021

(51) Int. Cl.
*A61B 17/06* (2006.01)
*A61B 17/04* (2006.01)

(52) U.S. Cl.
CPC .... *A61B 17/06109* (2013.01); *A61B 17/0482* (2013.01)

(58) Field of Classification Search
CPC .......... A61B 17/0482; A61B 17/06109; A61B 2017/00946; A61B 2017/06042
See application file for complete search history.

(56) References Cited

U.S. PATENT DOCUMENTS

| 5,222,977 A * | 6/1993 | Esser ............... A61B 17/06004 606/144 |
| 5,618,290 A | 4/1997 | Toy et al. |
| 2016/0175003 A1* | 6/2016 | Kafiluddi ........... A61B 17/3401 604/158 |

FOREIGN PATENT DOCUMENTS

| BR | 10-2019-023355-9 | 5/2021 |
| WO | WO 2015/089034 | 6/2015 |

OTHER PUBLICATIONS

U.S. Appl. No. 17/678,273, filed Feb. 23, 2022, De Faria et al.
"Protector Meniscus Suturing Set," Arthrex, date unknown, retrieved May 17, 2022 from https://www.arthrex.io/products/AR-4060S, 3 pages.

* cited by examiner

*Primary Examiner* — Mohamed G Gabr
(74) *Attorney, Agent, or Firm* — Sheridan Ross P.C.

(57) ABSTRACT

The present invention refers to a reusable meniscus suture device that comprising a handle for handling the device; a single-part needle comprising an elongated solid body which extends from the handle and a free end opposite the handle endowed with a cutting tip; and at least a portion of the elongated body gradually tapers in thickness towards the cutting tip, forming a portion of greater thickness in the region near the handle, and a portion of lesser thickness in the region near the tip, and wherein the portion of lesser thickness is malleable and curvable; and wherein the tip of the distal end has a lumen for the passage of the suture thread.

15 Claims, 8 Drawing Sheets

MENISCUS SUTURE DEVICE

CROSS-REFERENCE TO RELATED APPLICATION

This application claims the benefit of Brazil Patent Application No. BR102019023355-9 filed Nov. 6, 2019, the entire disclosure of which is incorporated herein by reference.

The present invention refers to a meniscus suture device for medical use in surgeries to repair lesions in the meniscus, which may be sterilized and reused, and which provides greater operating facility to the surgeon.

DESCRIPTION OF THE STATE OF THE ART

Various types of meniscus suture devices used in surgical procedures are known in the state of the art, yet most of them are disposable and have angular limitations that hinder the suture of totally or partially broken menisci. Normally, these devices have a handle whereby they are manipulated by the surgeon, and a body connected to the handle, the body being endowed with an internal cannula and a needle tip. The suture thread traverses the cannula of the body up to the needle tip, enabling the thread to be conducted to the meniscus. During the suture process, the needle tip pierces the tissue of the meniscus, passing the suture thread through it.

An example of a meniscus suture device is known from the "Protector Meniscus Suturing Set", by Arthrex. This device is used to suture the meniscus with the inside-out type techniques. The device comprises a disposable curved cannula connected to a plastic handle for handling by the surgeon. The plastic handle has a hole communicating with the inside of the cannula. Additionally, the device comprises a nitinol needle in the form of a separate part, which has a pointed end, and an opposite end comprising a connection which is traversed by a suture thread. At the moment of the suture, the cannula is positioned with the opposite end to the handle next to the tissue to be stitched. The pointed end of the needle is introduced into the handle hole and pushed through the handle and the cannula, until it comes out at the end of same near the tissue to be stitched. Then, the pointed end of the needle pierces the tissue and is pushed through it, until the end comprising the connection where the suture thread is coupled also passes through the tissue. The displacement of the needle inside the suture device can be performed with the assistance of a pusher, which may, thereafter, be used to pull the pointed end of the needle through the opposite side of the pierced tissue and the suture thread itself. This disposition of the suture device requires doing one stitch at a time, repeating this same operation described herein. Additionally, to assure the feasibility of displacing the needle inside the curved cannula, it must be malleable and fine, which makes it more fragile and less resistant.

The suture device is divulged in a kit jointly with a tool for adjusting the curvature of the cannula, which is used to mold the curvature of the end of the cannula depending on the suture technique to be used and the position of the tissue to be sutured, accommodating different anatomical variations.

However, this device of the state of the art has a very high cost and presents various problems relating to its usability. For example, it is common in surgical procedures for the connection of the needle where the line passes to break during the suture, meaning the line gets lost inside the knee of the patient and a new needle is required to look for the old line and resume the procedure.

In this type of device, it is also common for problems to occur relating to the curvature of the cannula and to the resistance of the needle. Despite allowing the adjusting of the curvature of the cannula where the needle passes, this deformation is irreversible because the cannula is hollowed, such that any external deformation causes the deformation in its inner diameter. The deformation in the inner diameter may cause an obstruction, meaning the needle cannot pass through. Therefore, if a mistake is made when preparing said curvature, the device is rendered unusable and has to be discarded. Even though the cannula is correctly curved, there is still the risk that the needle tip of the device may break, as it is malleable and fragile. Accordingly, several devices are needed for a single surgery, which makes the procedure costly and hard to access for patients.

Therefore, the state of the art does not comprise suture devices whose format is adjustable to the position and to the suture technique (inside-out, all-inside, outside-in) and to the location of the tissue to be sutured, that are reusable, resistant, and which enable the surgeon to do various stitches at a time.

OBJECTIVES OF THE INVENTION

The objective of the present invention is to provide a meniscus suture device that is reusable and has a low manufacturing cost, which enables the surgeon to do various stitches at a time, accelerating the procedure, and which assures the feasibility of performing inside-out, outside-in and all-inside sutures at different points of the meniscus.

BRIEF DESCRIPTION OF THE INVENTION

The objectives of the invention are achieved by means of a reusable meniscus suture device comprising a handle for handling the device, a single-part needle comprising an elongated solid body which extends from the handle and a free end opposite the handle endowed with a cutting tip, and at least a portion of the elongated body gradually tapers in thickness towards the cutting tip, forming a portion of greater thickness in the region near the handle, and a portion of lesser thickness in the region near the tip, wherein the portion of lesser thickness is malleable and curvable and wherein the tip of the distal end has a lumen for the passage of the suture thread.

The device is sterilizable and its handle is made of nitacetal and its elongated body is made of stainless steel. In one embodiment, the lumen has a circular format. In another embodiment, the lumen is in the form of a cutting which extends as far as a side edge of the needle tip.

BRIEF DESCRIPTION OF THE DRAWINGS

For improved understanding, the characteristics and advantages of the present invention will be presented and described jointly with its respective drawings, which illustrate.

DETAILED DESCRIPTION OF THE INVENTION

The meniscus suture device, object of the present invention, is used in repair surgeries (suture) of the meniscus, preferably by arthroscopy.

As can be seen in the embodiment of the invention shown in FIGS. 1 to 5, the meniscus suture device comprises a handle 10 for professional handling of the device and a single-part needle. The needle comprises an elongated solid body 20 which is connected, and which extends from the handle 10 and a free end opposite the handle, endowed with a cutting tip 21, for piercing and application of the stitches on the patient.

Preferably, the handle 10 is made of nitacetal. The choice of nitacetal to form the handle 10 is because the material is light, relatively low in cost and easily sterilizable.

The elongated body 20 is, preferably, made of stainless steel, which is the material used normally in surgical instruments and is also sterilizable.

According to the invention, at least a portion of the elongated body 20 gradually tapers in thickness towards the cutting 21 tip, forming a portion of greater thickness in the region near the handle 10, and a portion of lesser thickness in the region near the tip 21.

This tapering may begin at various positions of the elongated body 20, depending on the format most suited to the type of surgery to be carried out. For example, in the two embodiments of the invention illustrated in this application, the tapering begins at approximately mid-length of the elongated body.

A portion of lesser thickness of the needle is malleable and curvable. Since the thickness is reduced, this portion near the cutting tip of the needle 21 presents lower resistance, which gives it a certain malleability, enabling the tip 21 of the distal end to be molded with the curvature to be determined as the need arises. This characteristic is particularly relevant, since the position where the surgical procedure is carried out varies according to the lesion site. A malleable tip whose curvature can be molded enables the surgeon to adapt the device to a position that facilitates the procedure and minimizes the risks.

Even more advantageously, this portion of lesser thickness near the needle tip which is malleable and curvable can be remolded and curved several times, without damaging the needle. This is because the needle is solid, so there is no worry about preserving the format of the inner opening for passage of the suture thread of the needle, contrary to that which occurs in the state of the art. Moreover, this portion of lesser thickness configured and sized so as to maintain sufficient resistance to enable it to be molded and curved several times, without losing the rigidity needed to pierce the tissue of the meniscus to be stitched.

Figure 1:
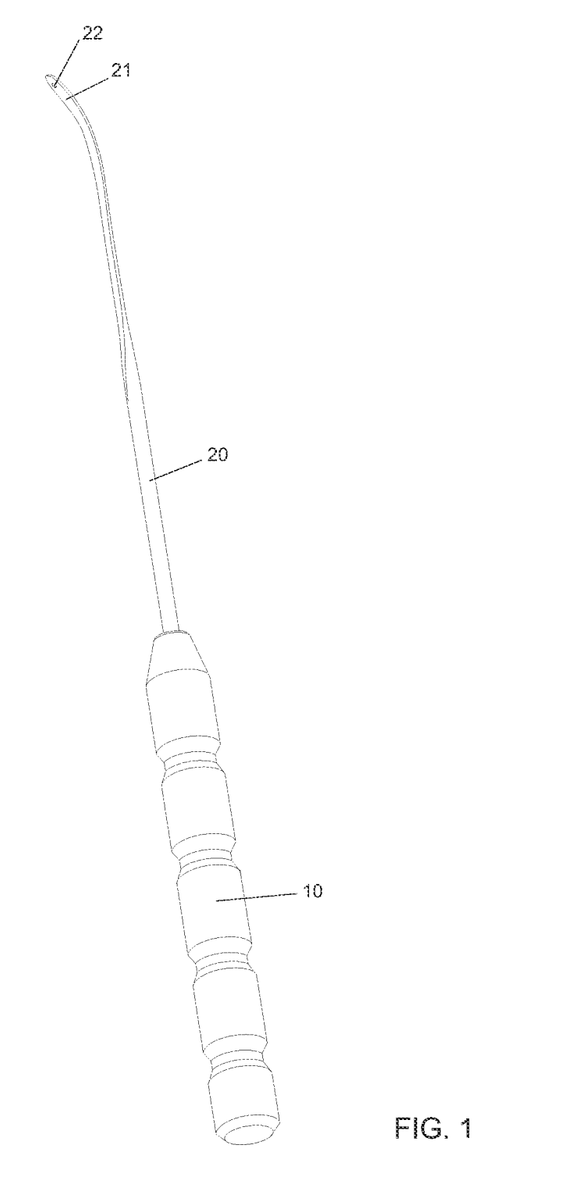
FIG. 1—a perspective view of a first embodiment of the meniscus suture device according to the invention, with a circular lumen.
Figure 2:
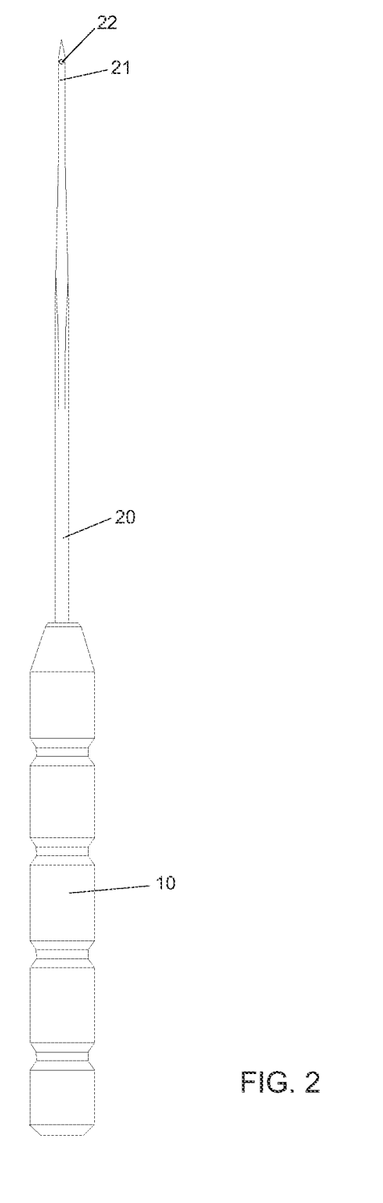
FIG. 2—a front view of the meniscus suture device shown in FIG. 1.
Figure 3:
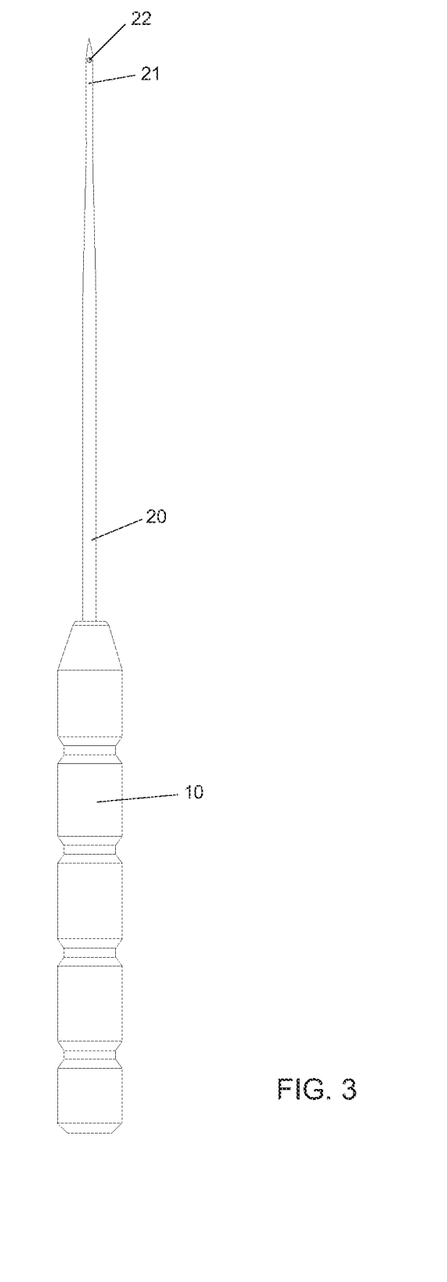
FIG. 3—a rear view of the meniscus suture device shown in FIG. 1.
Figure 4:
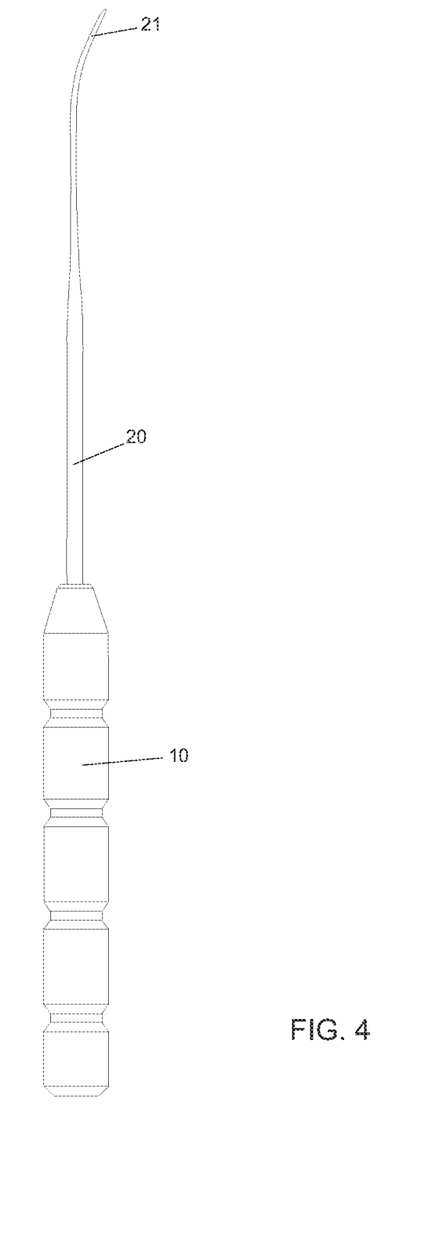
FIG. 4—a side view of the meniscus suture device shown in FIG. 1.
Figure 5:
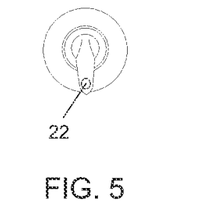
FIG. 5—a top view of the meniscus suture device shown in FIG. 1.

It is possible to see in FIG. 1 the variation in thickness of the elongated body 20, as well as the curvature at the tip 21, according to this first embodiment of the invention. It is also possible to note that the tip 21 of the needle is sharp and cutting, meaning the needle is capable of piercing the patient's meniscus in order to do the stitches.

The needle also has a lumen 22 at the tip 21, through which the suture thread passes. Therefore, the suture thread is already disposed at the portion of the needle that will pierce the tissue, whereby eliminating the need for the entire body of the needle to traverse the tissue of the meniscus, as occurs in the state of the art.

Since a single needle is used throughout the surgical procedure and the same carries the line at its hole end, this suture device enables various stitches to be done in sequence, it being suffice for the suture line used to have sufficient length. All that is needed is to perform the movement to do each stitch, without changing the line.

The lumen 22 may have different formats according to the surgeon's need. In the embodiment of the invention shown in FIGS. 1 to 5, the lumen 22 has a circular format through where the suture thread is passed to be guided by the suture device through the meniscus.

Figure 6:
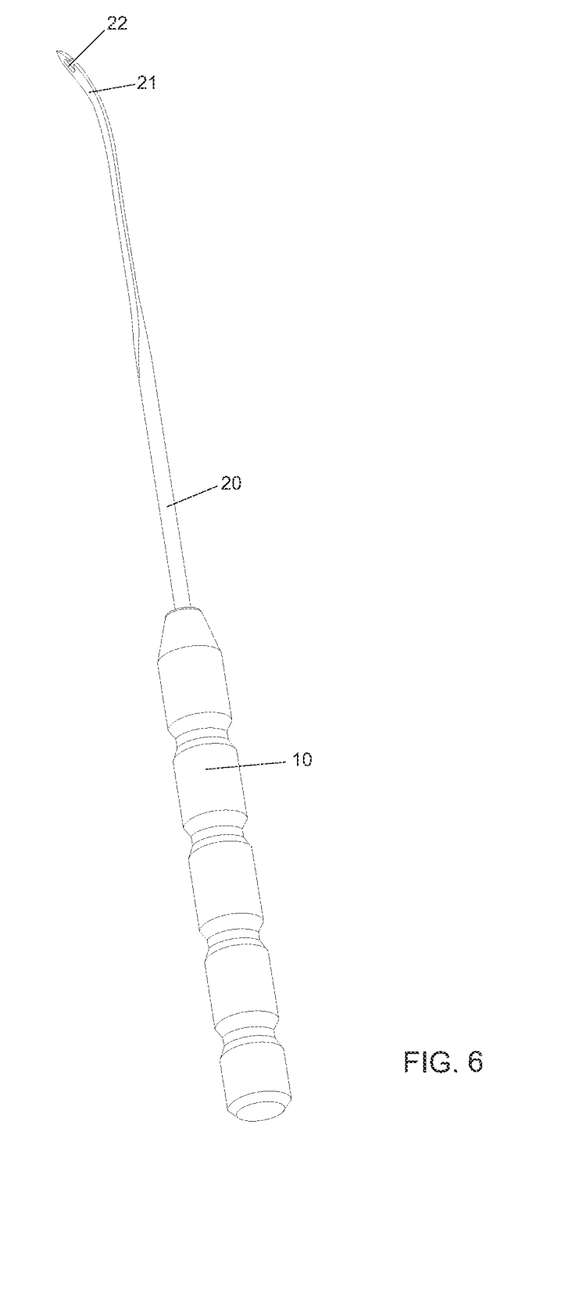
FIG. 6—a perspective view of a second embodiment of the invention, wherein the meniscus suture device has a cutout rectangular lumen.
Figure 7:
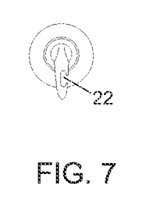
FIG. 7—a top view of the meniscus suture device shown in FIG. 6.
Figure 8:
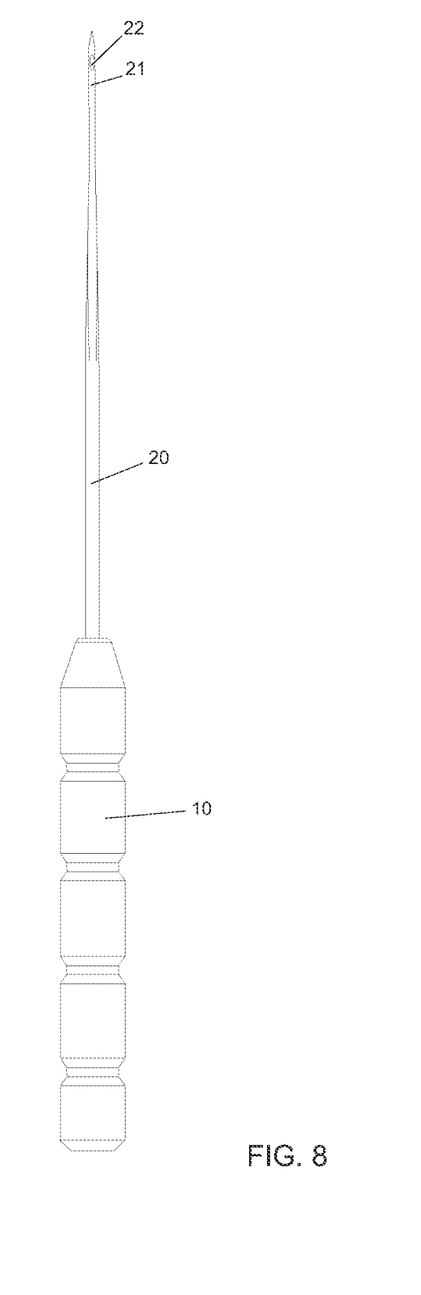
FIG. 8—a front view of the meniscus suture device shown in FIG. 6.

In the embodiment of the invention shown in FIGS. 6 to 8, the lumen 22 is in the form of a cutting which extends as far as the edge of one of the sides of the needle tip. In this embodiment, the cutting has a rectangular format. This embodiment is particularly interesting, since the lumen endowed with cutting enables the needle to recover the thread if it is lost, with the lumen 22 acting as a "hook".

The present invention as described enables a same suture device to be used in a surgical procedure, sterilized and reused. Additionally, the device according to the invention is more resistant and durable than those known in the state of the art, since the needle is comprised of a single part, including the body of the device and the cutting tip, being made entirely of stainless steel, and this material is more resistant than the nitinol used in the needles of the state of the art. The malleability is provided by the finer thickness of the region near the needle tip, but it is sized so as to allow its remolding into varied curvatures several times. These two characteristics are relevant, as they reduce the general cost of surgeries, since there is no excessive cost with the purchase of various disposable and easily breakable devices, different to the suture devices of the state of the art which are disposable and easily breakable.

As discussed previously herein, today, when repair (suture) procedures are carried out on the meniscus, a plurality of disposable apparatuses is acquired due to the low resistance, as the risk of breakage of the device from the state of the art during a surgical procedure is considerable.

Additionally, as the tip of the device is moldable and can take on formats with varied curvatures, the device can be used to perform "inside-out", "outside-in" and "all inside" sutures, differently to the devices of the state of the art which, normally, can only be used for "inside-out" sutures, or just for "outside-in" or "all-inside" sutures. The device of the present invention is, therefore, particularly advantageous, by enabling the three techniques to be performed, giving greater freedom and flexibility for the surgeon to adopt the most suitable technique for each case.

Lastly, the suture device according to the present invention slightly reduces the time and the complexity of this type of meniscus suture surgery, since the procedure for doing each stitch of the suture is much simpler and quicker, to the extent that various stitches can be done in sequence quickly.

Having described an example of preferred embodiment, it should be understood that the scope of the present invention encompasses other possible variations, not being limited solely to the content of the accompanying claims, potential equivalents being included therein.

The invention claimed is:

1. A reusable meniscus suture device, comprising:
   a handle for handling the device;
   a single-part needle comprising an elongated solid body which extends from the handle and a free end opposite the handle endowed with a cutting tip;
   wherein at least a portion of the elongated body gradually tapers in thickness towards the cutting tip, forming a portion of greater thickness in the region near the handle, and a portion of lesser thickness in the region near the tip, and wherein the portion of lesser thickness is malleable and curvable and wherein the tip of the free end has a lumen for the passage of the suture thread,
   wherein the tapering begins at approximately mid-length of the elongated body, the portion of greater thickness having a first cross-sectional area and a first cross-sectional shape, and the portion of lesser thickness having a second cross-sectional area and a second cross-sectional shape, and wherein the first cross-sectional area is greater than the second cross-sectional area, and the first cross-sectional shape is distinct from the second cross-sectional shape.

2. The device, according to claim 1, wherein the handle is made of polyoxymethylene (POM).

3. The device, according to claim 2, wherein the elongated body is made of stainless steel.

4. The device, according to claim 2, wherein the lumen has a circular format.

5. The device, according to claim 2, wherein the lumen is in the form of a cutting which extends as far as a side edge of the needle tip.

6. The device, according to claim 2, wherein the suture device is sterilizable.

7. The device, according to claim 1, wherein the elongated body is made of stainless steel.

8. The device, according to claim 7, wherein the lumen has a circular format.

9. The device, according to claim 7, wherein the lumen is in the form of a cutting which extends as far as a side edge of the needle tip.

10. The device, according to claim 7, wherein the suture device is sterilizable.

11. The device, according to claim 1, wherein the lumen has a circular format.

12. The device, according to claim 11, wherein the suture device is sterilizable.

13. The device, according to claim 1, wherein the lumen is in the form of a cutting which extends as far as a side edge of the needle tip.

14. The device, according to claim 1, wherein the suture device is sterilizable.

15. The device, according to claim 1, wherein the first cross-sectional shape is substantially circular, and the second cross-section shape is substantially rectangular.

* * * * *

UNITED STATES PATENT AND TRADEMARK OFFICE
CERTIFICATE OF CORRECTION

| | | |
|---|---|---|
| PATENT NO. | : 11,589,861 B2 | Page 1 of 1 |
| APPLICATION NO. | : 16/799372 | |
| DATED | : February 28, 2023 | |
| INVENTOR(S) | : José Leonardo Rocha de Faria, Bernardo Augusto Rocha de Faria and Alan de Paula Mozella | |

It is certified that error appears in the above-identified patent and that said Letters Patent is hereby corrected as shown below:

On the Title Page

After the "(65) Prior Publication Data" section, insert Item (30):
--(30) Foreign Application Priority Data Nov. 6, 2019 (BR) ................... 102019023355-9--

Signed and Sealed this
Eleventh Day of July, 2023

Katherine Kelly Vidal
*Director of the United States Patent and Trademark Office*